United States Patent [19]

Wakatake

[11] Patent Number: 4,647,432

[45] Date of Patent: Mar. 3, 1987

[54] AUTOMATIC ANALYSIS APPARATUS

[75] Inventor: Koichi Wakatake, Koganei, Japan

[73] Assignee: Japan Tectron Instruments Corporation Tokuyama Soda Kabushiki Kaisha, Tokuyama, Japan

[21] Appl. No.: 540,980

[22] Filed: Oct. 11, 1983

[51] Int. Cl.$^4$ .......................................... G01N 35/04
[52] U.S. Cl. ...................................... 422/64; 422/67; 422/100; 73/863.32
[58] Field of Search .................... 422/63-67, 422/100, 73; 356/246; 141/168, 169; 73/863.32

[56] References Cited

U.S. PATENT DOCUMENTS

| | | | |
|---|---|---|---|
| 3,143,393 | 8/1964 | Des Hons | 422/67 X |
| 3,489,521 | 1/1970 | Buckle et al. | 422/65 |
| 3,504,376 | 3/1970 | Bednar et al. | 422/66 |
| 3,826,622 | 7/1974 | Natelson | 422/65 |
| 4,091,323 | 5/1978 | Landis | 422/64 |
| 4,113,436 | 9/1978 | Werder et al. | 422/65 |
| 4,263,256 | 4/1981 | Morle | 422/65 |
| 4,268,477 | 5/1981 | Herzstark | 422/67 |
| 4,313,735 | 2/1982 | Yamashita et al. | 422/65 |
| 4,338,279 | 7/1982 | Orimo et al. | 422/64 |
| 4,346,056 | 8/1982 | Sakurada | 422/64 |
| 4,363,781 | 12/1982 | Akamatsu et al. | 422/100 |
| 4,451,433 | 5/1984 | Yamashita et al. | 422/64 |

FOREIGN PATENT DOCUMENTS

| | | | |
|---|---|---|---|
| 54-161388 | 12/1979 | Japan | 422/64 |
| 55-1551 | 1/1980 | Japan | 422/64 |
| 55-121150 | 9/1980 | Japan | 422/63 |
| 56-168553 | 12/1981 | Japan | . |
| 57-16360 | 1/1982 | Japan | 422/63 |
| 2131168 | 6/1984 | United Kingdom | 422/64 |

OTHER PUBLICATIONS

The Paramax Analytical System-American Dade, ©1981.

Primary Examiner—Barry S. Richman
Assistant Examiner—Michael S. Gzybowski
Attorney, Agent, or Firm—Armstrong, Nikaido, Marmelstein & Kubovcik

[57] ABSTRACT

A novel automatic analysis apparatus in which a plurality of reaction tubes, according to the necessity, are held by a pair of turret tables disposed in predetermined spaces, and a reaction tube exchange means held between the tables automatically exchanges the reaction tubes held by one table for those of the other table at a predetermined position without stopping the rotation of the tables, and thereby achieves a charging operation, a measuring operation and a cleaning operation necessary for analysis of a specimen, such as blood, reagent or the like at a high speed with high precision and, in addition, facilitates measurement of an urgent specimen such as for operation.

10 Claims, 14 Drawing Figures

AUTOMATIC ANALYSIS APPARATUS

BACKGROUND OF THE INVENTION

This invention relates to a medical precision measuring apparatus for analyzing a collected blood specimen biochemically or immunologically, and particularly relates to an apparatus for analyzing substances present in a blood specimen by optically measuring the specific color produced by the reaction of blood and a reagent or a diluent.

As a prior art of this type, the apparatus disclosed in Japanese Patent-Application Laid Open No. 56-168553 (Appln. No. 55-73210) is well known.

However, in prior apparatuses of this type there are some defects as follow.

First, due to the fact that reaction tubes which are held in a reaction portion are suspended in one cylindrical reaction table, the number of reaction tubes is determined according to the diameter of the table used. Therefore, in order to improve the through-put capacity of an analysis apparatus, it is necessary to enlarge the diameter of the table to increase the number of the reaction tubes. However, if the table is enlarged, the apparatus itself becomes overly large-sized which necessitates a large space for establishment thereof. In addition, the use and manufacture of drive and stop controls of the reaction table become difficult.

Second, since such a series of operations as charging of and measuring a specimen and the cleaning of a reaction tube are conducted in one revolution of the reaction table, a rotary speed of the reaction table is relatively reduced for ensuring each of those operations and it takes a long time to treat one specimen.

Third, this speed limitation brings to prior systems another defect, i.e., making the urgent measuring of specimen in such a case as an emergency operation. Such difficult a defect does not satisfy the recent requirement for accelerating the optical measuring using 2 reagents at a high speed and with high precision.

SUMMARY OF THE INVENTION

One of the primary objects of the present invention is to provide a novel automatic analysis apparatus for optically measuring and analyzing the specific color produced by the reaction of blood and reagents.

A more particular object of the present invention is to provide an automatic analysis apparatus optically measuring a specific color produced by a reaction of blood and a reagent comprising at least two turret-type reaction tube holding means placed in parallel for holding a plurality of reaction tubes in predetermined spaces thereof, a reagent vessel holding means disposed in coaxial relation with the reaction tube holding means and radially holding a plurality of reagent vessels, a driving means for transferring the regent vessels to a predetermined charging position, a charging means for charging reagents in the vessels to the reaction tubes, a reaction tube exchange means for exchanging the reaction tubes held in one of the reaction tube holding means for the reaction tubes held in the other reaction tube holding means, a driving means for transferring the reaction tube and an optical measuring means for continuously optically measuring specimens in the reaction tubes during while the reaction tubes are being held in the other reaction tube holding means. In one reaction tube holding means, blood and the reagent being charged to the reaction tube are held, and in the other of said reaction tube holding means, the reaction tube being transferred and being subjected to the measuring is held.

Another object of the present invention is to provide an automatic analysis apparatus wherein one of said reaction tube holding means includes pipette means having a plurality of pipettes held in a turret pipette holder for intermittently moving the pipettes from a blood sucking position to a pipette cleaning position through a blood charging position.

Still another object of the present invention is to provide an automatic analysis apparatus wherein the reagent vessel has a rectangular projecting portion formed at one part of the vessel and communicating with an interior of the vessel, the projecting portion having a discriminating body formed for encoding the kind of the reagent in the vessel or the like, and wherein reagent vessel holding means includes a detecting means disposed in the center of the reagent vessel holding means for differentiating the liquid level in a vessel and data about the kind of liquid substance or the like in the vessel by descending and ascending along the projecting portion of the vessel.

A further object of the present invention is to provide an automatic analysis apparatus wherein the reagent charging means are disposed in inner peripheral sides of the respective reaction tube holding means and the reagent charging means includes a transferring means for transferring the reagent vessel containing the reagent to the charging position through a reading means reading data from the discriminating body.

A still further object of this invention is to provide an automatic analysis apparatus wherein the reaction tube exchange means for exchanging the reaction tubes is placed between the reaction tube holding means placed in predetermined spaces and includes a clamping means for clamping the reaction tube being transferred in a predetermined position and an exchange means for exchanging the reaction tubes by rotating in a 180° arc.

A still further object of the present invention is to provide an automatic analysis apparatus wherein the detecting means is adapted to detect a liquid level contained in the reagent vessel by receiving at a light-receiving element light generated from a luminous element and transmitting same through a projecting portion of light-transmitting material formed on the reagent vessel.

A still further object of the present invention is to provide an automatic analysis apparatus wherein the detecting means comprises a luminous element and a receiving element for receiving a light generated from the luminous element and reflected by the projecting portion and is adapted to detect a liquid level contained in the reagent vessel by comparing the differences in regulation a voltage converted from the light received by the light-receiving element

BRIEF DESCRIPTION OF THE DRAWINGS

These and other advantages and features of the present invention will hereinafter appear for purposes of illustration, but not of limitation, in connection with the accompanying drawings, in which like numbers refer to like parts throughout, and of which.

DESCRIPTION OF PREFERRED EMBODIMENT

Figure 1:
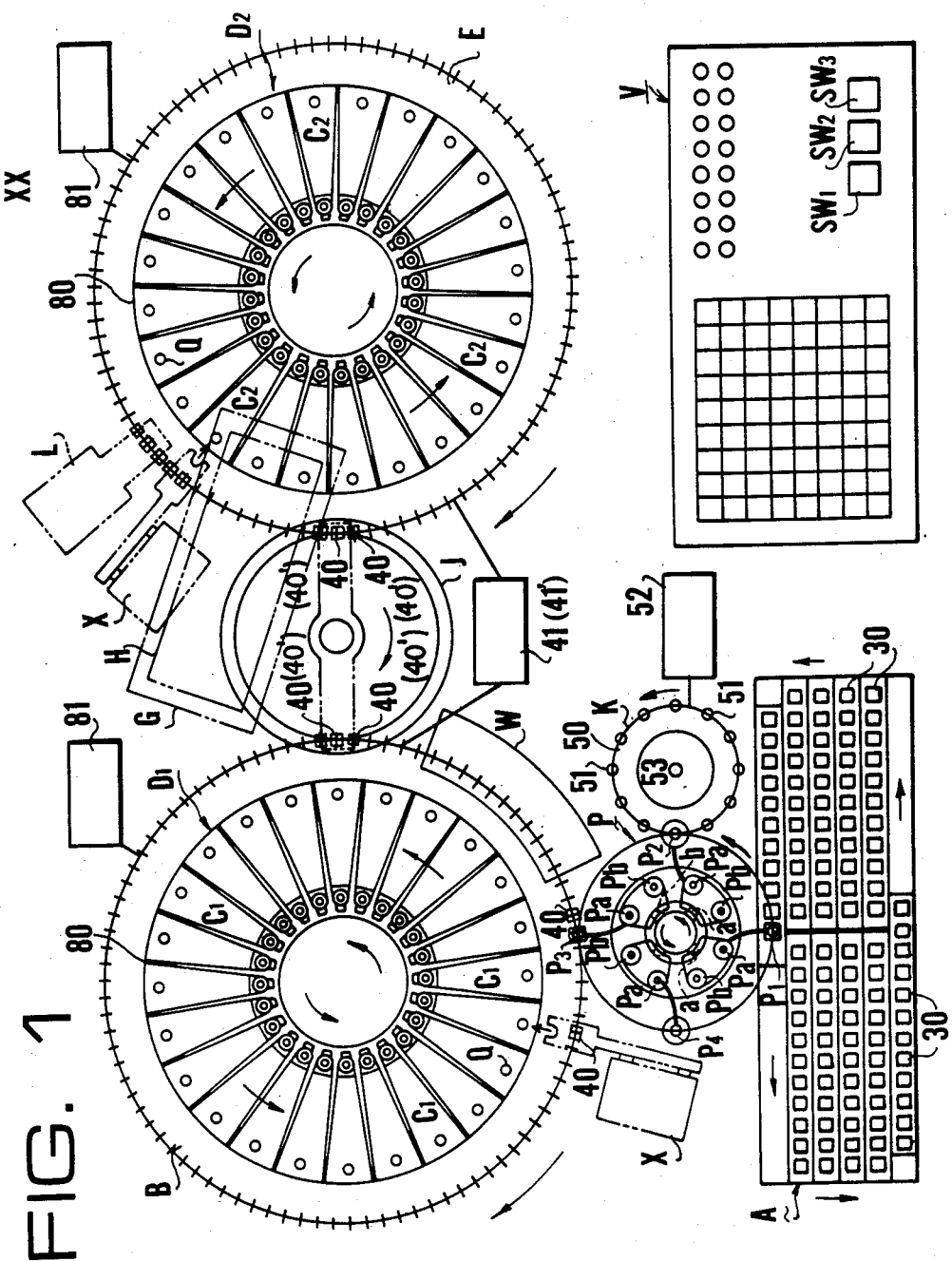
FIG. 1 is a schematic top plan view illustrating a preferred embodiment of an automatic analysis apparatus made in accordance with the present invention.

Referring now to the drawings, and in particular to FIG. 1, the present invention is illustrated, by way of example, as being embodied in a biochemical automatic analysis apparatus, a plurality of sample cassettes A for ordinary specimens holding a plurality of cups 30 each of which may contain a predetermined amount of a specimen, such as blood, for measuring (in the embodiment illustrated, one sample cassette contains 10 cups for ordinary specimens and one cup for a comparative specimen), a sampler K holding specimens for emergencies, a pipette device P sucking up the ordinary specimens or the emergency specimens in a predetermined amount in a predetermined position for injection into a reaction tube 40, a turret-like feeder B holding a plurality of the reaction tubes 40, a reagent device D, disposed along the inner periphery of the turret-like feeder B in coaxial relation with the feeder B and having on a turret-like holder 80 a plurality of reagent bottles C which are removably put in the reagent device and which contain reagents corresponding to measuring items, a reaction tube exchange device J for transferring the reaction tubes 40 charged with a predetermined amount of ordinary or emergency specimens and a predetermined amount of reagents of predetermined types, from the feeder B to a measuring turret table E, an optical device G for measuring specific color of the specimen contained in the reaction tube 40 which is held in the turret table E for measurement, a digital processor H for indicating and memorizing data determined by the optical device G and a cleaning device W for cleaning the reaction tubes after a series of the above-described measuring operations are finished.

Figure 2:
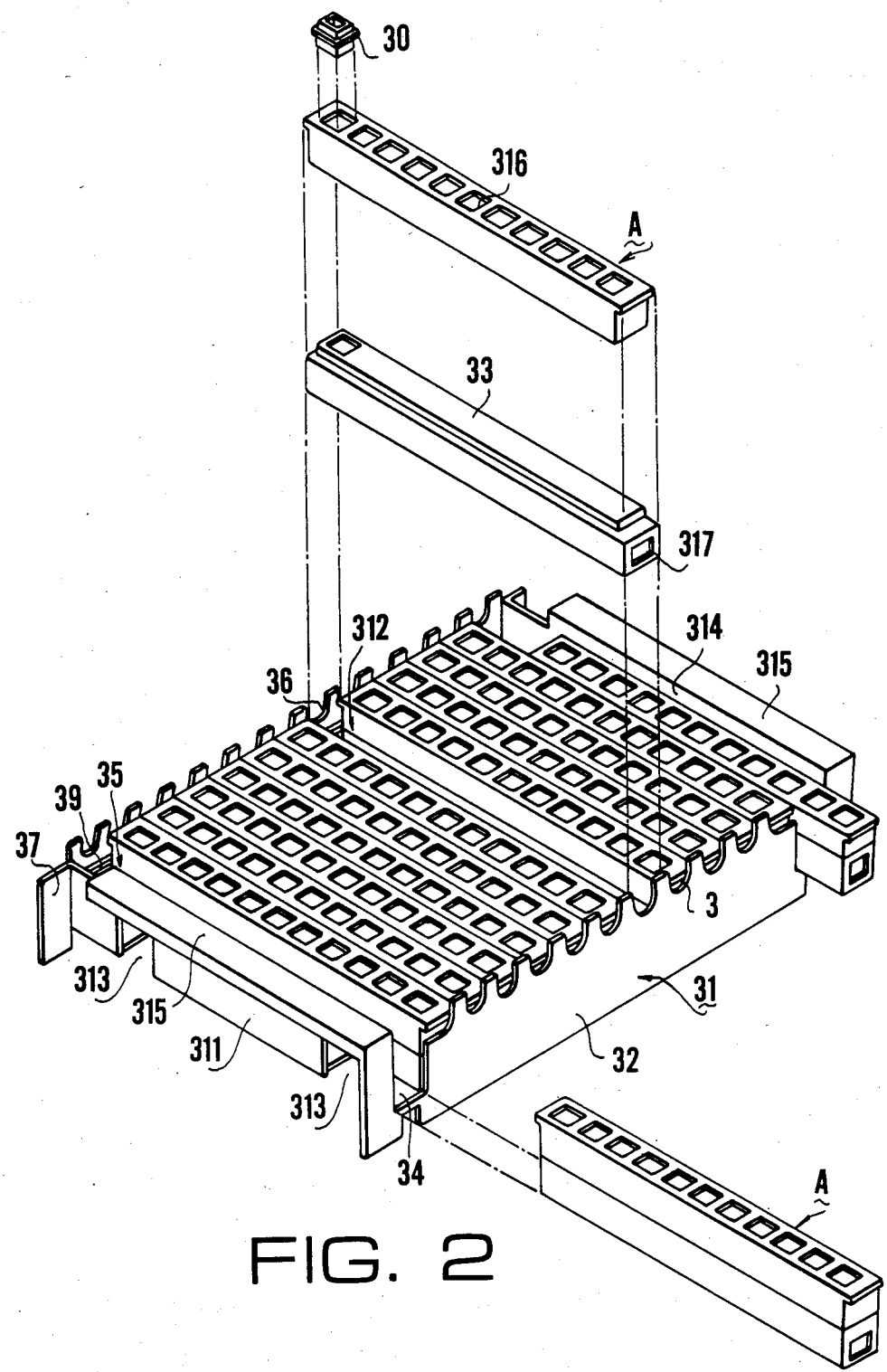
FIG. 2 is a perspective, partial, combined fragmentary view illustrating a preferred embodiment of a sample cassette and a cassette tray made in accordance with the present invention.

A plurality of the above sample cassettes A for ordinary specimens are held in parallel relation in a cassette tray 31 as illustrated in FIG. 2.

Figure 4:
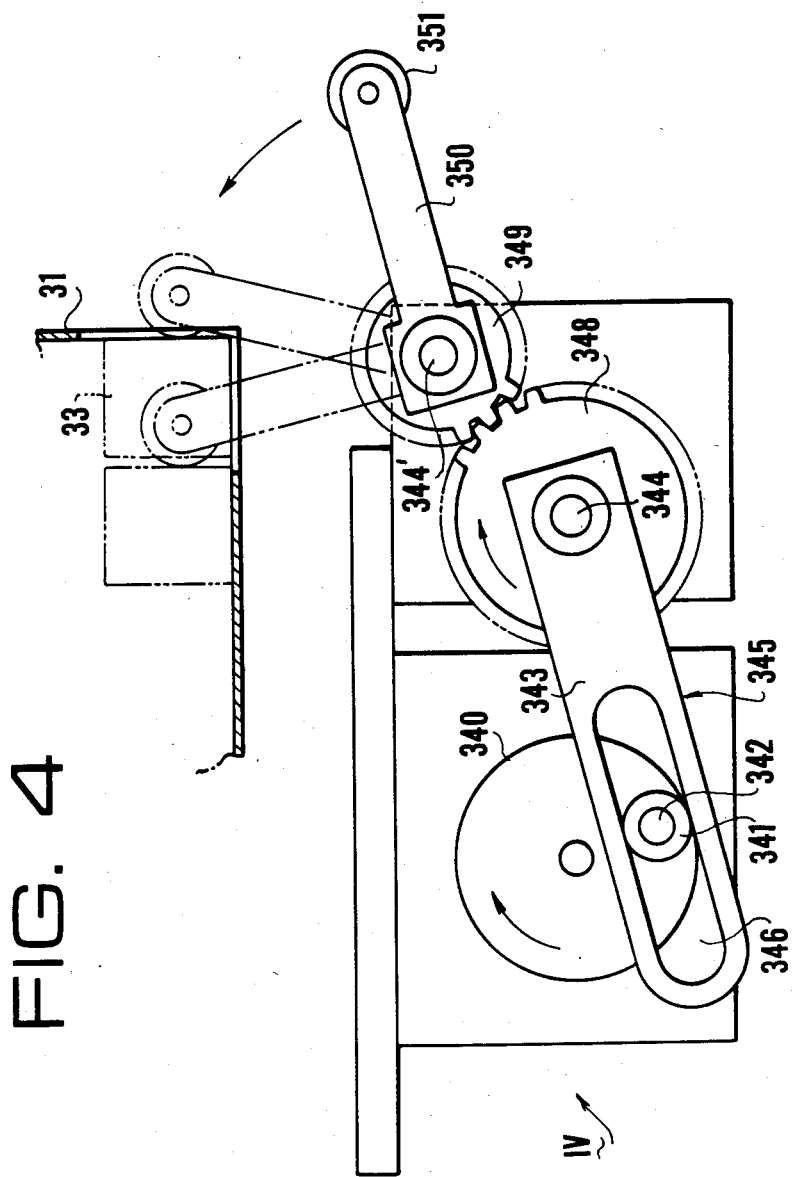
FIG. 4 is a vertical sectional view illustrating a longitudinal feed mechanism of the sample cassette shown in FIG. 2.

This cassette tray 31 is formed in the shape of a rectangular box and at the front and back ends thereof has a cut out portion (notch) 34, 35 formed in a shape of rectangle so as to introduce thereinto the sample cassette A for an ordinary specimen mounted on a stand 33 as illustrated in FIG. 2. In addition, there are provided in the cassette tray at the top edge portions of the opposite side walls 32 and 37, a plurality of cut out portions 36 each having generally the shape of a half circle corresponding to the width of the ordinary specimen sample cassette. At the inner surfaces and along the lower portions of the right and left side walls 32 and 37, guide portions 39 are provided to slidably guide the sample cassette A along a longitudinal direction of the walls 32 and 37. Near an abutting portion of a front wall 311 and a bottom wall 312 are provided generally rectangular holes 313 and 313 through which arms of a longitudinal feeding means IV (as shown in FIG. 4) of the sample cassette A move. At upper portions of the front wall 311 and rear wall 314 are provided grip portions 315 and 315 for carrying the cassette tray 31. The cassette tray 31 is removably fitted in a sampler. In FIG. 2, the sample cassette A is formed in a generally rectangular parallelopiped configuration and has the same length as the width between the side walls 32 and 37 of the cassette tray 31.

Further, at an upper surface of the sample cassette A, eleven (11) rectangular holes 316 are provided in which the above described cups 30 are removably fitted. A number 33 designates a stand which removably fits in a lower end portion of the sample cassette A and has the same length as the sample cassette. An upper portion of the stand 33 is of two stage structure so as to fit in this upper sample cassette at the stage.

In addition, at the upper end portion of the stand 33 there is provided a light transmitting hole for reading a code (not shown) and at the bottom portion of the stand is provided a hook hole 317 according to the cutout portion of the hole 316 of the sample cassette A. This hook hole 317 is used as a stopper when the sample cassette A is cross-fed.

Thus, when the ordinary specimen sample cassettes A are to be arranged in the cassette tray 31, at first specimens (serum) to be measured are extracted and charged in each cup 30. Next, the sample cassettes A are put in the stands 33 to build up a two stage structure, then are sequentially disposed in order in the cassette tray 31 to fill the interior of the cassette tray 31 with the sample cassettes A.

The cassette trays 31, so prepared with the ordinary specimen sample cassettes A, are push-in fitted to the sampler from a predetermined position.

When the analysis apparatus is switched on, the sample cassette A in the front line of the cassette tray is first moved from the cutout portion 35 in the crossed arrow direction (shown in FIG. 1) intermittently together with the stand 33 by a sample cassette cross feeding means IH (shown in FIG. 3) so that each of the cups 30 successively reach a position $P_1$ where a sample is sucked up according to necessity. This cross-movement of the sample cassette A in the front line of the tray interlocks a sample cassette disposed adjacent to the cassette A and pushes the adjacent sample cassette transversly at the same speed. When the sample cassette in the front line reaches the adjacent tray, a longitudinal feeding means IV (shown in FIG. 4) of the sample cassette is put into operation and extends a sending-out arm through the holes 313 to push the stand 33 in the last line of the cassette tray in a forward motion.

At this time, all of the ordinary specimen sample cassette A in the cassettes tray 31 slidably advance with the stand 33 in spaces of the width of one cassette. When the last sample cassette in the tray advances, the cross-feeding means IH is again put into operation and the same action as above described is repeated, whereby new sample cassettes are successively transferred to the cassette tray 31 through the cutout portion 34.

Figure 3:
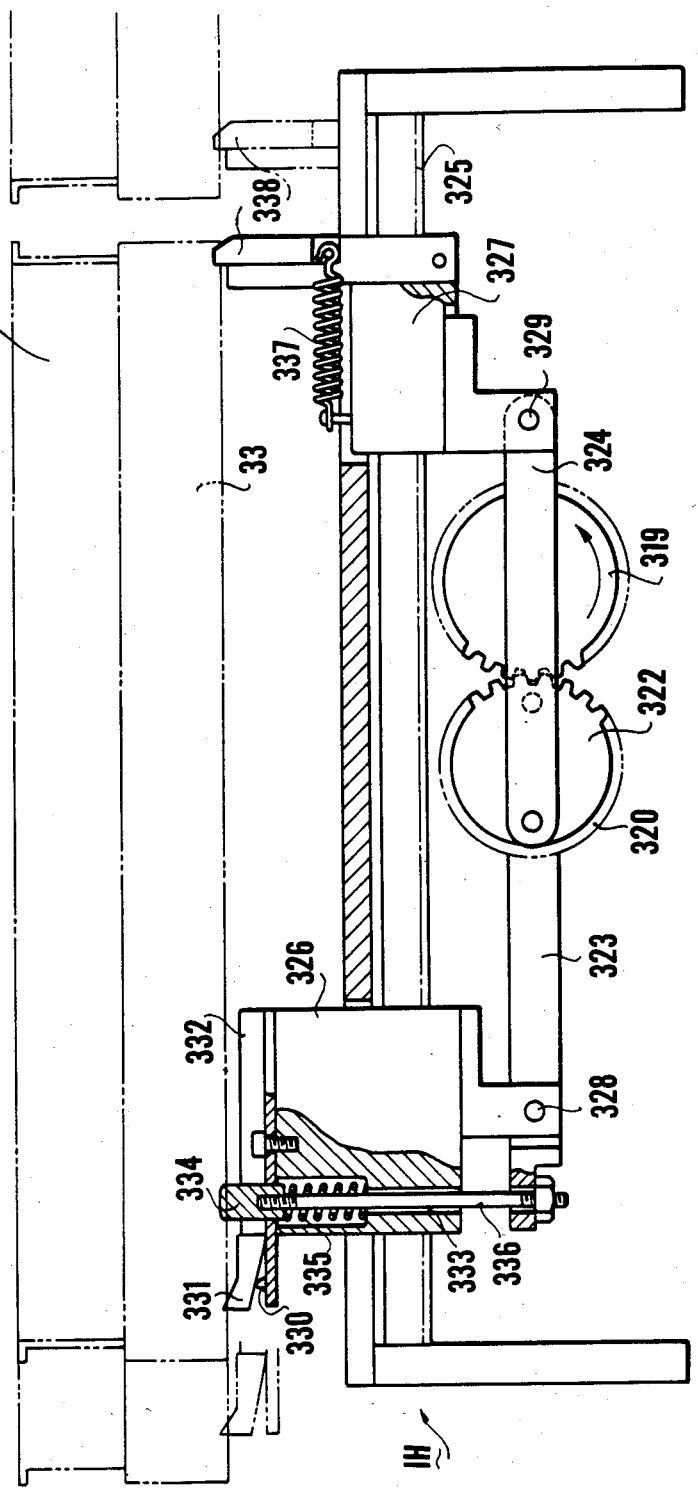
FIG. 3 is a vertical sectional view illustrating a cross-feed mechanism of the sample cassette shown in FIG. 2.

Referring to FIG. 3, in the cross-feeding device IH comprising a part of a sample cassette feeding means, power from a motor is first transmitted to a gear 319 and next to a gear 320. In the gear 320, a driving ring 322 is provided so as to interlock to the gear 320 and one end each of the links 323 and 324 are mounted on the gear 320 and the driving ring 322 in a diagonal line in opposite sides of a supporting pillar. The other end of the link 323 mounted on the gear 320 is rotatably supported by a pin 328 at a lower portion of a first slider 326 which is slidably mounted on two parallel horizontal axes 325 and the link 324 mounted on the driving ring 322 is rotatably supported by a pin 329 at a lower portion of a second slider 327 which is slidably mounted on the horizontal axes 325 as described above. Both the first and second sliders are supported by the horizontal axis 325 extending into throughholes made in center portions of the bodies thereof.

On a tip end of the first slider 326 is mounted a claw 331 which is urged by a compression coil spring 330. The claw 331 has an upwardly tilting configuration. A number 332 designates a claw holder. Further, the first slider 326 has a throughhole 333 which perpendicularly penetrates into the first slider, at a rearward position of the claw 331. The shaft 336 penetrating into the throughhole 333 has at an upper portion thereof a chip 334 urged by compression coil springs 335 and is connected to a tip end of the link 323 at a lower portion thereof.

The second slider 327 has at a tip end thereof a claw 338 which is urged by tension springs and formed in a position tilting in the same direction as that of the claw 331.

The claws 331 and 338 of the cross-feeding device IH, so formed, engage the hole 317 formed in the bottom of the stand 33 to enable the cross-feeding of the sample cassette A.

When a signal from the cross-feeding device is input to a control device (CPU), a motor drives to rotate the gears 319 and 320 one full revolution in the arrow direction as illustrated in FIG. 3. While the gears 319 and 320 rotate 180°, the links 323 and 324 move in the opposite directions from each other and with this movement, the two sliders 326 and 327 also slide in the opposite directions from each other. In this case, the claw 331 engages the hole 317 formed in the bottom of the stand to allow the stand 33 to slide to a cross direction at intervals of one cup. When the slider 326 returns in position, the claw 331 is pushed downwardly by virtue of the weight of the stand 33 and the sample cassette A and returns in position. When the gear 320 rotates one revolution, he claw 331 fits in the next hole of the stand. The chip 334 projects into the hole 317 while the slider 326 moves forwardly, but when the slider 326 returns, the chip returns in a downwardly pulled state rather than the normal state since a tip end of the link 323 connected to the shaft 336 descends through a pin 328 as a supporting point.

The claw 338, mounted on the second slider 327 for vertical swinging movement, is caused to swing downwardly by means of tension spring 337 while slider 327 slides rearwardly. When slider 327 is fully rearward, the claw 338 thus rearwardly swung engages a hole 317 in one end face of the next stand 33 in the first row of the cassette tray, and when the slider 327 returns in position, it allows the stand 33 to slidably move one step. This return motion of the slider 327 interlocks with the slider 326. Thus, the claw 331 of the first slider 326 and the claw 338 of the second slider 327 each independently move the stand 33 and accordingly delivers the sample cassette A integral with the stand 33 in the cross direction step by step. At the time when this cross movement is terminated, a signal to the longitudinal feeding device IV as shown in FIG. 4 is input. Referring to FIG. 4, in the longitudinal feed device IV, power from a motor provides a rotational motion to a crank 340. At one end of the periphery of the crank 340, a ball bearing 341 is provided through a bearing pin 342. This ball bearing 341 slides along an inner periphery of an elongated slot 346 which is provided at a tip end of a rocker arm 345. The rocker arm 345 has a base end 343 fixed to a shaft 344 as a bearing shaft. The opposite end of the shaft 344 rotates depending on a rotation of the bearing 347 and interlocks with the up and down movement of the rocker arm 345. A flat gear 348 having a large diameter is fixed to this shaft 344 and intermeshes with a flat gear 349 having a small diameter which is fixed to a shaft 344' provided in parallel to the shaft 344. The shaft 344' has two delivery arms 350 fixed thereto with a suitably adjusted angle and rotates depending on a rotation of a bearing. The roller 351 of the tip end of arm 350 is rotatable and relieves the contact resistance at the time of the delivery of the stand 33 disposed in the last line of the cassette tray 31. Therefore, when a longitudinal feeding signal is input to the computer provided, a motor is driven and the crank 340 rotates in an arrow direction full one revolution. With this rotation, the ball bearing 341 rotates on the crank 340 sliding along the elongated slot 346 provided in the rocker arm 345, whereby the rocker arm 345 rocks with the bearing pin as a center supporting axis in upward and downward directions. As the ball bearing 341 moves upwardly, the flat gear 348 rotates in an arrow direction illustrated in FIG. 4, and the delivery arm 350 swivels upwardly depending on the rotation of the flat gear 349 having a relatively small diameter. In the swiveling process, the roller 351 provided in the tip end of the delivery arm 350 abutts in engagement with the rear side surface of the last stand 33 in the cassette tray 31 and in successive swiveling, allows the stand 33 to slide upwardly. The delivery arm 350 pushes the stand 33 continuously until the tip end of the rocker arm 345 reaches the upward position at the maximum. The flat gears 348 and 349 rotate in opposite directions from each other meshing with the movement of the rocker arm 345, whereby the delivery arm 350 downwardly swivels and returns to the original position. The distance in which the stand 33 slidably advances by one swivel of the delivery arm 350 is predetermined. At the time the operation of the longitudinal delivery is finished, a signal is transmitted to the cross-feeding means and similar operation as described before is repeated.

Thus, each of the ordinary specimen sample cassettes A mounted on the stands 33 is moved a cross direction and a longitudinal direction by the feeding device which is driven by the signal input in predetermined intervals and the specimen (serum) is injected into each of the reaction tubes by a pipette P in a predetermined sucking position $P_1$.

In the drawings of FIGS. 1 and 2 illustrated as one embodiment of the present invention, the ordinary specimen sample cassette A contains eleven (11) cups of specimens at one time and the specimens are contained in cups 30 each having the same configuration. Ten (10) cups of the specimens counting from the right hand contain human serum as the ordinary samples and the last one cup contains a precision control substance such as serum of an animal, artificial serum or the like.

Thus, it is preferred that the measurement is made in a combination of ten (10) ordinary samples and one precision-control substance to obtain a more precisely measured value. However, it is not necessary to prepare such a precision-control substance in every specimen sample cassette. It may be arranged in every other line or every six lines of the sample cassettes.

Both the ordinary samples and the control specimen are measured under the same conditions, that is, by being sucked by the pipette P in the sucking position, injected into the reaction tubes 40 and optically measured by the optical device G. In addition, a thus measured value is transmitted to a signal treating device H and automatically undergoes a data processing. The measured result of the ordinary sample is treated with consecutive numbering different from the result in the precision control specimen. Thus, since the number of the ordinary specimen samples is a multiple of the number ten (10), the relationship of the data and the sample can be easily understood. The measured result of the precision control specimen is compared with a standard value of the control specimen in the digital processor H to automatically detect the precision of the control specimen at the measuring time in the analysis apparatus, whereby the measured value of ten (10) specimens of the ordinary samples are modified. Thus, the value derived in the periodical measurement of the control substance amends the measured value of the ordinary sample before the next control specimen is measured.

Further, the reliability of the measured value over the entire measurement may be cleared from the degree of scattering of the measured value of the control specimens in the measuring time obtained by comparing the total of the measured values and a standard value of the control specimen.

In addition, in the present invention it is not necessary to prepare the control sample in every sample cassette A as before described. If an empty cup, without containing the control specimen is set in the sample cassette, the position thereof is memorized previously in the digital processor H and quickly fed by a skip means (not shown) when the empty cup is transferred to the sample sucking position, whereby a cup containing an ordinary specimen sample is quickly transferred to the sucking position saving time. The skip means is so constructed that the sample cassette cross-feeding means IH actuate to feed the ordinary sample cassette continuously in two steps at once.

The sampler K is provided for urgent specimens, and removably abuts against the pipette P as illustrated in FIG. 1.

A specimen necessitating emergency analysis, for example, for data about an emergency operation, is contained in a plurality of vessels 51 which are held in a turret plate 50. The turret plate 50 rotates intermittently about a shaft 53 by a driving means 52. When the vessel 51 is transferred to a position $P_2$ for sucking the urgent sample in the pipette means P, the pipette P actuate to suck up a predetermined amount of the sample. The operation in this case is controlled by the digital processor so that the driving operation of the ordinary specimen sample cassette A is immediately stopped. After all of the urgent specimens are analyzed, the driving means of the ordinary specimen automatically starts to work. To facilitate the analysis of the urgent specimen, as shown in FIG. 1 it is enough to change the switch selected in the operation panel from a switch $SW_1$ for ordinary specimens to switch $SW_3$ for urgent specimens $SW_2$ as shown in FIG. 1 is a stop switch.

The pipette means P comprises 4 pipettes held in a turret pipette holder in a predetermined spaces shown in FIG. 1 and is controlled so as to intermittently move in a 90° arc by a motor (not shown) and a conventional cam mechanism or the like.

Particularly, as the pipette holder moves, the pipettes suck up a predetermined amount of an ordinary specimen at position $P_1$, suck up a predetermined amount of an urgent specimen at positoin $P_2$, and inject the ordinary or urgent specimens into the reaction tubes 40 in a predetermined amount at position $P_3$. Then the pipette holder moves to position $P_4$ to clean up the pipettes and sequentially returns to position $P_1$ again.

In addition, each of the pipettes is fitted with a sucking pump Pa and a discharge pump Pb as shown in FIG. 1, which each engage cams for sucking and discharging the specimens in position to actuate under the control of the digital processor.

When the ordinary specimens are sucked and charged, the sucking pump Pa and the cam a for each of the pipettes engage each other at the position $P_1$ as shown in a solid line in FIG. 1, and the discharge pump Pb and the discharge cam for each of the pipettes engage each other at the position $P_3$. When the urgent specimens are sucked and discharged, the cam a for sucking the specimens moves so as to engage the sucking pump Pa at the position $P_2$ and a cam b is arranged to engage the discharge pump Pb at the position $P_3$. When the sucking and charging of the urgent specimens are finished, the sucking cam automatically returns to the sucking position $P_1$ for the ordinary specimens from the position $P_2$ by an instruction signal from the digital processor H.

Thus, the reaction tubes 40 filled with the ordinary or urgent specimens are held in the feeding means, in the shape of a turret which is intermittently rotated through the driving means 41 (such as Geneva gear mechanism), and transferred to a position for charging a reagent, where a first reagent is charged to the reaction tubes 40 through the first reagent means $D_1$ according to a measurement item.

Figure 5:
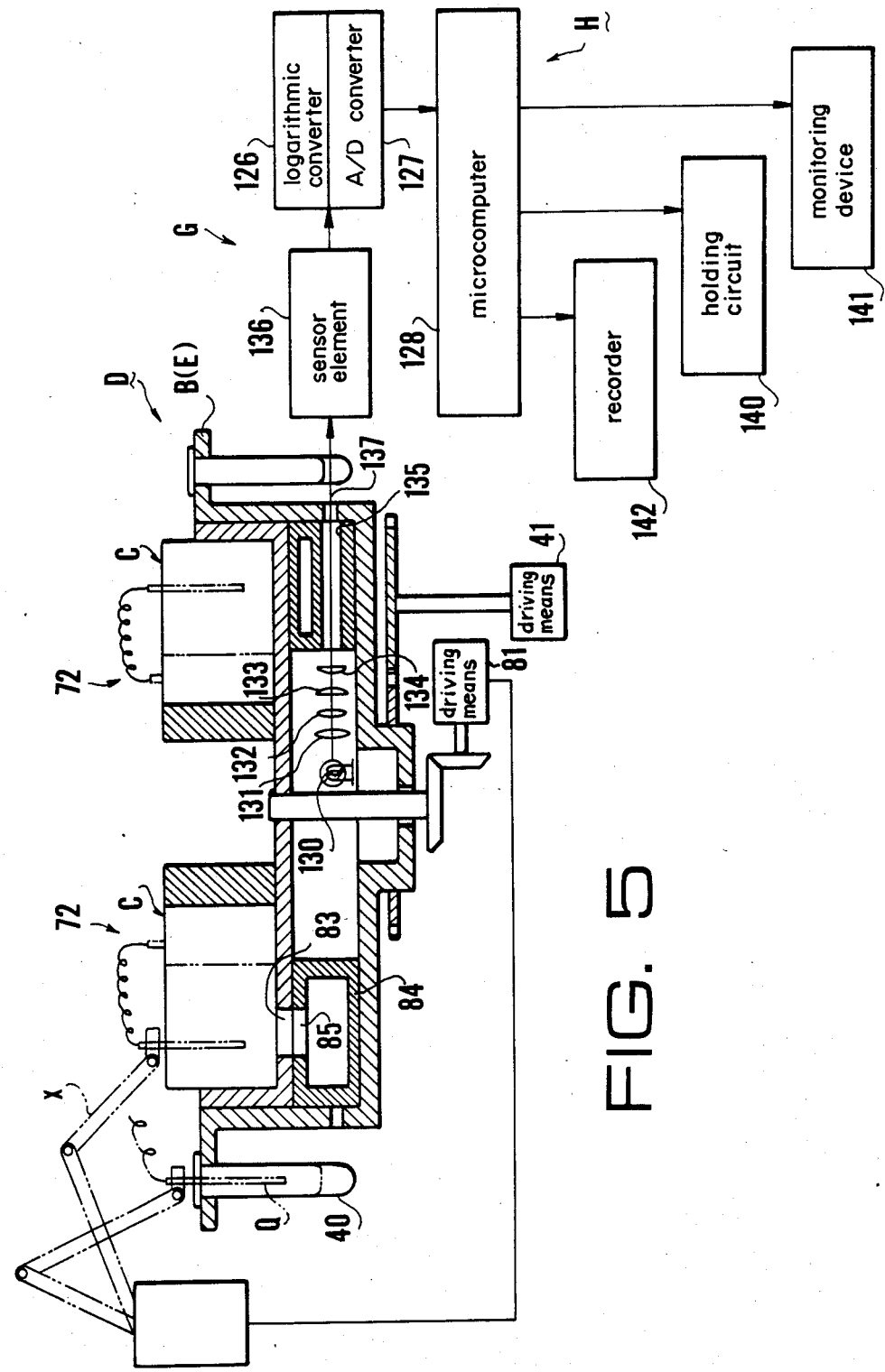
FIG. 5 is a vertical sectional view illustrating a combined structure of a feeder, a sampling device, an optical device and a digital processor.
Figure 6:
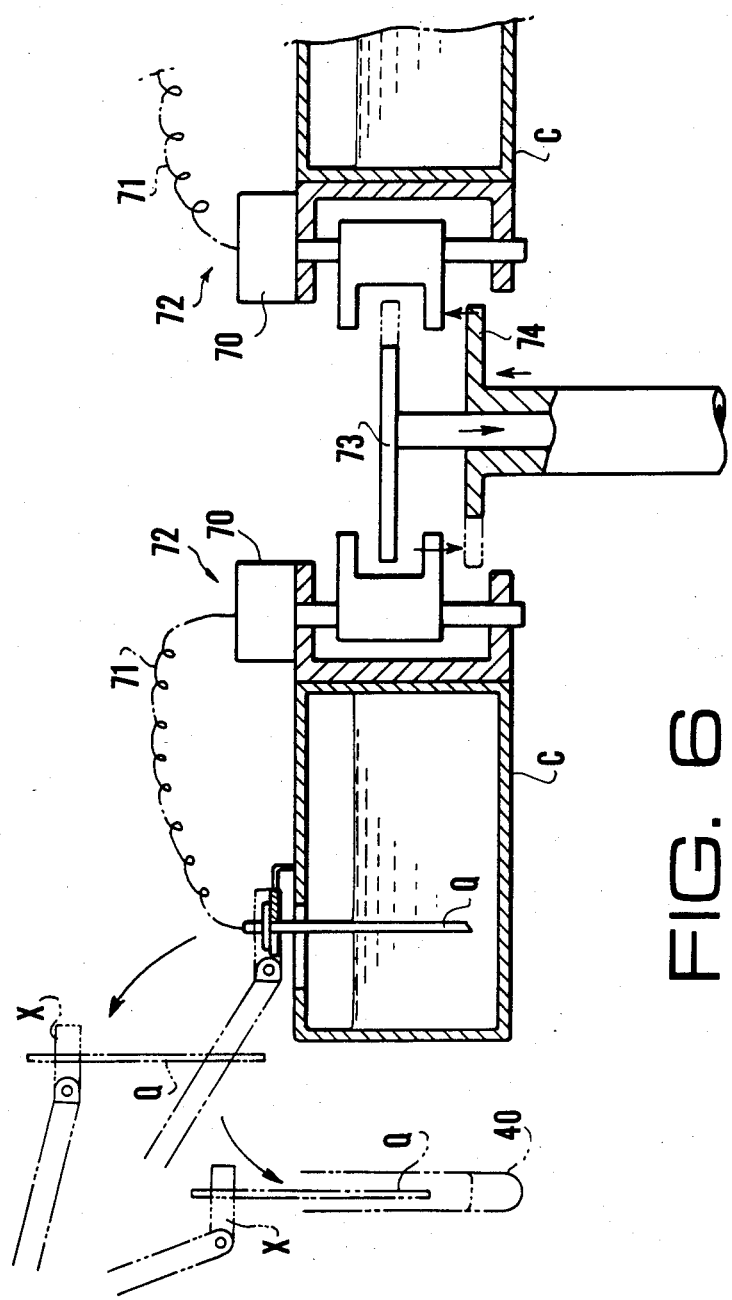
FIG. 6 is an enlarged illustrative view of each device shown in FIG. 5.

Referring to FIGS. 5 and 6, the first reagent device $D_1$ comprises a reagent bottle C made of a light-transmitting material at least at the bottom thereof, and mounted on a holder having the shape of a turret and made of a light-transmitting material, a driving means 81 transferring the reagent bottle C to the reagent charging position at a high speed, and a reagent pipette Q picking up the reagent from the reagent bottle C and charging it to the reaction tube 40. Particularly, the turret holder 80 is disposed in the interior of the feeding means B in coaxial relation and on the turret holder 80, a plurality of the reagent bottles C are radially removably mounted and in the reagent bottle C various reagents are contained according to analysis items. Thus, the turret holder 80 is controlled by the driving means 81 so as to rotatably transfer the reagents necessary for analysis.

The reagent bottle C described above comprises a reagent bottle containing a reagent suitable for room temperature storage, for example, T.P., Z.T.T. or the like, and a reagent bottle containing such a reagent necessitating cool storage, for example GOT, GPT or the like. The reagent bottle for cool storage is disposed in an optional place of the turret holder 80. In the optional place a plurality of throughholes 83 are provided, elsewhere no hole is provided.

On a lower portion of the turret holder 80, a duct 84 made of a light-transmitting material is provided in coaxial relation with the turret holder 80. On an upper surface of the duct 84, a cool air supplying hole 85 communicating with the throughhole 83 is provided in predetermined spaces. The duct 84 is fixedly provided and does not rotate with the turret holder 80.

Therefore, a cooling medium flowing in the duck 84 flows from the air supplying hole 85 through the throughhole 83 to the bottom of the reagent bottle for cool storage to cool and preserve the reagent in the cooling reagent bottle. But because there are no through holes for passage of the cooling medium provided in the remaining portion of the turret holder 80 on which the reagent bottle for room temperature storage rests, this regent bottle is not cooled, and thus the reagent contained therein is free from recrystallization.

When the reagent bottle C containing the first reagent according to measuring items is transferred at a high speed to the position where the reagent is charged in the manner as described herein, the expansible reagent pipette Q mounted on each reagent bottle C is pulled out and led to the position of the reagent tube 40 by a holding means X thereby to charge the first reagent to the reaction tube 40 in a predetermined amount.

More particularly, at the rearward position of the reagent bottle C, there are provided, as illustrated in FIG. 6, a pump 70, a pipette tube 71 connected to and expansibly held by the pump 70 and a reagent pipette Q connected to the end of the pipette tube 71. The pump 70 engages a projecting portion of a cam 73 rotating directly and reversely and descends to suck up the first reagent. Then, the cam 73 releases the engagement with the pump 70 and returns to a neutral position. Thereafter, the arm of the holding means X extends to hold the reagent pipette, pulls the reagent pipette Q inserted in the reagent bottle C outwardly from the reagent bottle C, and leads it to the reaction tube 40, whereby the first reagent is charged to the reaction bottle 40 by the reagent pipette Q in a predetermined amount with the ascension of a second cam 74. At this time, the pipette tube 71 is led to a predetermined position since it is expansible. Thereafter, the holding means X releases the holding of the reagent pipette Q, while the reagent returns to the original position by means such as a spring or the like. Then, the pump 70 again engages the cam 73 and the same operation explained above is repeated.

Figure 7:
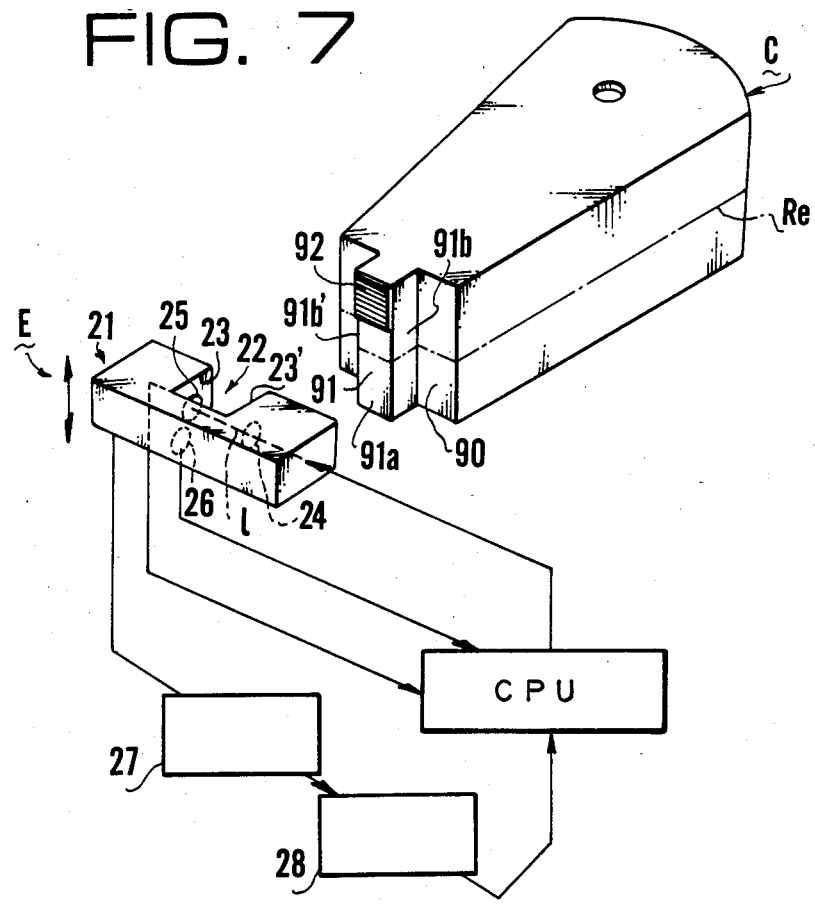
FIG. 7 is a schematic perspective view illustrating a back portion of a reagent bottle and a reading means in corresponding relation to the back portion of the reagent bottle made in accordance with the present invention.

As illustrated in FIG. 7, the reaction bottle C is of a generally rectangular configuration with an arc at one side thereof and has a rectangular projecting portion 91 communicating with the interior of the reaction bottle C on one side opposite to the arc side thereof. The projecting portion is made of an excellent light-transmitting material. In a front surface of the projecting portion at an upper end portion 91a not concerned with detection of a liquid amount, there is provided a discriminating body in which kinds and manufactured dates of the reagents contained in the bottle or the like are coded as a bar code, binary code or the like.

A detector as illustrated at E in FIG. 7 is disposed in an inner peripheral side of the reagent means D as illustrated in FIG. 1 and is adapted not to participate in the rotation of the reagent device. The detector E comprises a detector bracket 21 lifting along the projecting portion 91 of the reagent bottle C at a predetermined speed, a luminous element 24 and a light receiving element 25 disposed in opposite side surfaces 23 and 23' or a recess 22 formed in the detector bracket 21, a known optical reading element 26 disposed in the bottom portion of the recess 22, and a potentiometer 28 discriminating an amount of the lifting movement of the bracket 21 by detecting a rotary angle of a driving means 27 which drives the bracket 21.

When the other reagent bottle C is transferred to and stopped at a reagent charging position, the detector E simultaneously starts to lift upwardly and detects the reagent kinds or the like and the amount of the residing fluid in the reagent bottle C and then the detected data is input to a control means (CPU).

More particularly, such detection may be conducted as follows. When the reaction bottle C to be detected reaches a predetermined position and stops, first the detector bracket 21 starts to lift upwardly in the state of removably fitting with the projecting portion 91, then a light 1 having a specific wave length from the luminous element 24 is simultaneously applied to the side wall 91b of the projecting portion 91. The applied light is transmitted through the walls from one side wall 91b to the other side wall 91b' and received by the light receiving element 25. The received light is converted to a voltage for input to the control means (CPU) by the light receiving element 25.

When the light 1 is transmitted through the reagent Re in the reagent bottle C, the amount of the light received by the receiving element 25 is attenuated due to an absorption into the reagent Re, but when the light is transmitted through an atmosphere in the reagent vessel C, the amount of the light received in the receiving light element 25 is great since absorption does not occur. The timing of change in those received lights, i.e. the variation in voltages of from less voltage to more voltage is compared with a rotary angle of the driving means 27 detected by a potentiometer 28, the height of the liquid amount is detected on the basis of the obtained data, an amount of the residing liquid is calculated by the control means (CPU) on the basis of the detected height, and the data is indicated in a display and is input to the control means.

The data relating to the reagent in the reagent bottle C is differentiated optically from the distinguishing display 92 by means of a conventional optical reading element 26 and input to the control means. The reagent device D is controlled by the driving means 81, 81 based on the obtained data.

Figure 8:
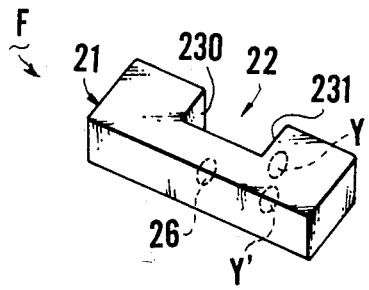
FIG. 8 is a perspective view illustrating another embodiment of the reading means made in accordance with the present invention.

Referring to FIG. 8, another embodiment F of the abovementioned detector E comprises a detector bracket 21 having a pair of detectors Y and Y' each including a luminous element and a light-receiving element and being disposed in vertical relation in predetermined spaces at one side 231 of a recess 22, and a conventional optical reading means 26 in the recess at either of those sides other than the side having Y and Y' disposed therein (at the bottom position in the embodiment illustrated in FIG. 7). The luminous element 24 (24') and the light-receiving element 250 (250') in detectors Y and Y' are disposed in predetermined spaces in the moving direction of the detector bracket 21 and the measuring light, such as ultraviolet light, which is emitted by the luminous element 24 (24') and reflected by the side surface of the projecting portion 91b may be received by the corresponding light-receiving element 250 (250').

The reason why the detectors Y and Y' are disposed at predetermined distances is to protect a liquid level detection from a variability of light volume converted voltage which is caused by a concave and convex flaw, or the like, present in the reflecting surface of the bottle C or a variability of light volume-converted voltage which is caused by an inaccuracy between the distances of the reflecting surface of the bottle and the sensor element. In order to increase a liquid level detecting precision, plural detecting bodies may be provided. Or, even one body is enough to function. Thus, the light emitted from the luminous element 24 (24') and reflected by the reflecting portion of the bottle (the side wall 91b in the embodiment of FIG. 7) is received by the corresponding sensor element 250 in the state as illustrated in FIG. 9 and converted to the corresponding voltage (In FIG. 9, only one detecting body is illustrated as one embodiment of the present invention).

Figure 9:
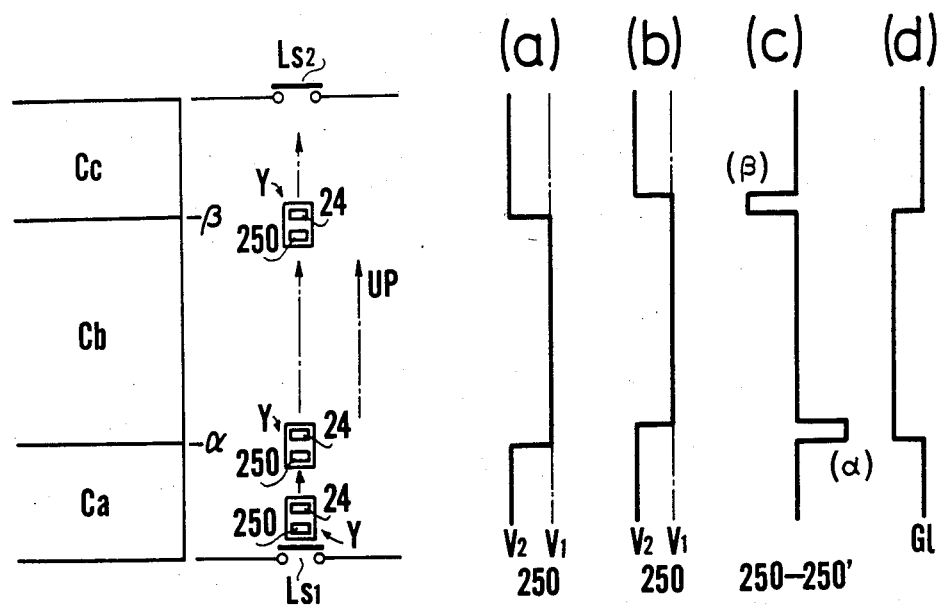
FIG. 9 is a diagrammatical view illustrating a working condition of the liquid level detector and an input condition of an electric signal in accordance with the present invention.
Figure 10:
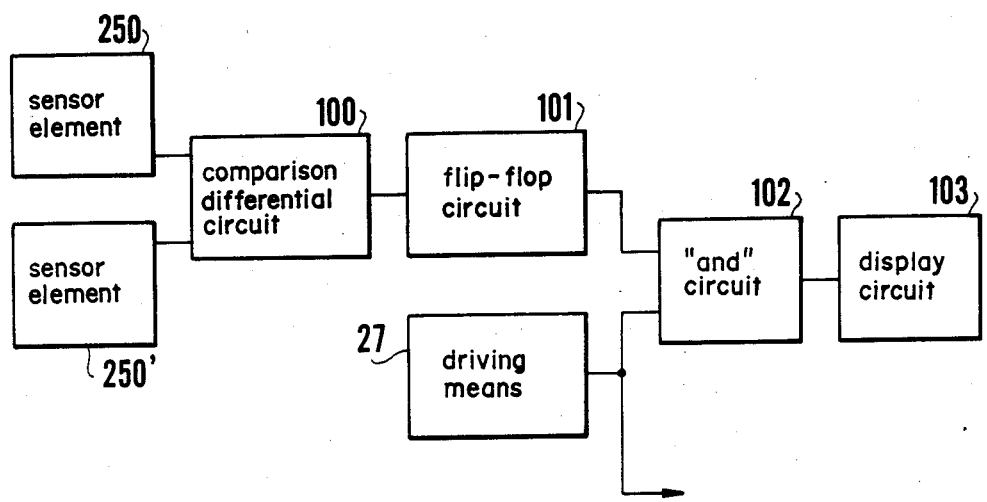
FIG. 10 is a block view illustrating the liquid level detector made in accordance with the present invention.

Referring to FIG. 9, as the light-receiving elements 250 and 250' move from a lower position Ca of the bottle to a reagent layer Cb, voltage signal levels, as shown at (a) and (b), of the corresponding sensor elements 250 and 250' move from a level $V_2$ to a level $V_1$ at a border line and thereafter as the sensor elements 250 and 250' move from a reagent layer Cb to an air layer Cc, voltage signal levels of the sensor elements 250 and 250' move from a level $V_1$ to a level $V_2$ at a border b. In this case, signal outputs from the sensor elements 250 and 250' are input to a comparison differential circuit 100 as illustrated in FIG. 10 as a difference in time between the distances of the sensor elements 250 and 250' since they are spaced from each other, whereby a direction of the differential voltage between the sensors is discriminated. Then the signal output is input to an "and" circuit 102 from a flip-flop circuit 101; the signal of the driving means 27, for example a pulse signal in case of a pulse motor, is input to the control means at the "and" circuit to carry out necessary operation, and is input to a display circuit 103. In FIG. 9, Ls2 denotes a lower limiting circuit and Ls1 is an upper limiting circuit. The liquid detection is made by a comparison operation of a gate time signal G1 and a pulse signal of the driving means 27. Further, the liquid detection may be made by a comparison operation of data obtained from detecting a rotary angle of the driving means by a potentiometer, and data relating to the voltage of the receiving element 250 and 250'.

Thus, the reaction tube 40 in which the specimen and the first reagent are charged is intermittently transferred to a predetermined position. The reaction tube 40 transferred to a predetermined position is further transferred to a measuring turret E through a reaction tube exchange means J.

The reaction tube exchange means J illustrated in FIG. 1 as one embodiment in accordance with the present invention lifts the reaction tube 40 held in the feeding means B and a reaction tube 40' held in the measuring turret E at the opposite end, rotates in a 180° arc, and then exchanges the reaction tube 40 for the reaction tube 40', so that the reaction tube 40 is placed in the position where the reaction tube 40' was held and the reaction tube 40' is placed in the position where the reaction tube 40 was held.

Figure 11:
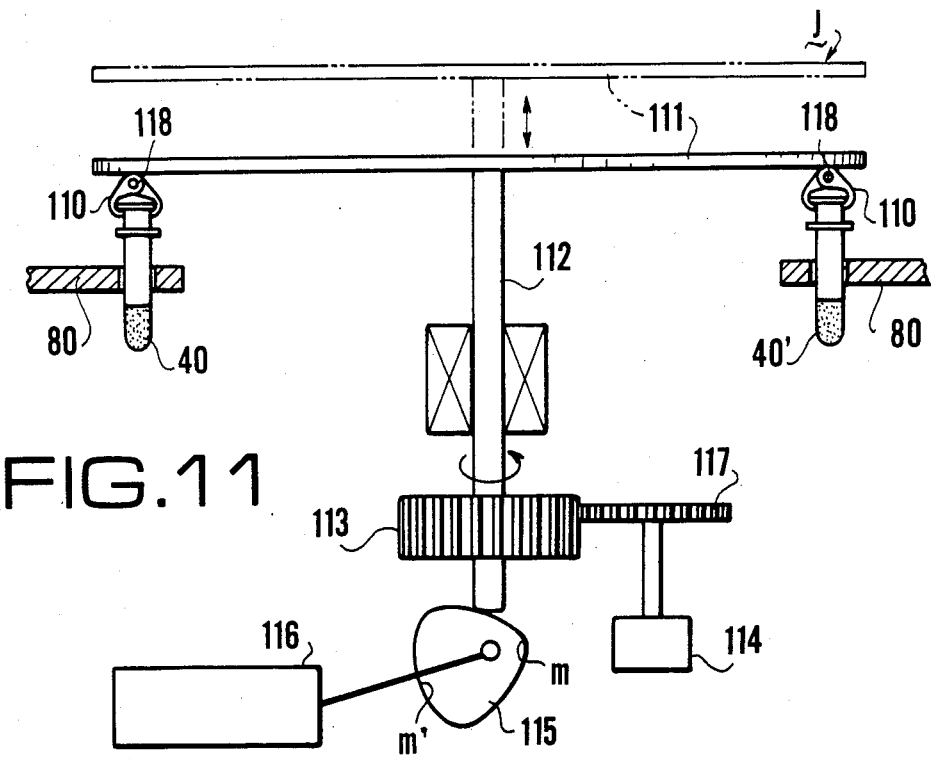
FIG. 11 is a schematic, front elevational view illustrating a reaction tube exchange device made in accordance with the present invention.

More particularly, the reaction tube exchange means J illustrated in FIG. 11 as one embodiment of the present invention comprises a supporting arm 111 having picking arms 110 at both ends thereof, a lifting rod 112 being fixed in the center of the supporting arm 111, a gear 113 being fixed on the outer periphery of the lifting rod at the lower end thereof, a driving means 114 allowing the lifting rod 112 to rotate in a predetermined direction in mesh with the gear 113, an eccentric cam 115 abutting a lower end of the lifting rod in engagement therewith, and a motor 116 rotating the eccentric cam 115.

Thus, the lifting arm 112 lowers to the lowest position at a shortest radius portion of the eccentric cam 115, rises to the highest position at the longest radius portion of the eccentric cam 115, fits in a gear 117 of the driving means 114 and is controlled by a driving force of the driving means 114 until the supporting arm 111 rotates in a 180° arc. The picking arms 110 are supported by a pin 118 and widen and narrow at the ends thereof. When the lifting rod 112 is positioned in the lowest position, the picking arms clamp the reaction tubes 40 and 40' through a conventional timing mechanism and after rotating in a 180° arc, release the clamping action.

Since the exchange of the reaction tubes 40 and 40' is executed during the transfer of the reaction tubes, without stopping the analysis apparatus, the measuring time is greatly shortened. In addition, since the structure of the analysis apparatus is simple, the failure is less and the maintenance is easy.

In this embodiment, the lifting control of the lifting rod is made by the eccentric cam 115 but the present invention is not limited by this case, for example an actuator may be applied.

The reaction tube 40, thus transferred to the measuring turret E, is further transferred to a position in which a second reagent is charged, by the measuring turret E.

Since the structure and effect of the second reagent device $D_2$ are similar to those of the first reagent device $D_1$, duplicate explanation is omitted here by using the same reference number designations.

If there is a measuring item not necessary to charge the second reagent, the signal for second charging is automatically cancelled.

The reaction tube 40, thus charged with the second reagent, is transferred to a stirring position. The stirring sequentially is made by a conventional supersonic vibration means L at the same time of exchanging the reaction tubes in such a manner as to not disturb the rotation of the measuring turret E, i.e., holding up the reaction tubes.

The optical device G disposed in the measuring turret E comprises a light beam from a light source lamp 120 bundled by lenses 131, 132, 133 and 134 advancing in a cylindrical portion 135, being transmitted through the reaction tube 40 from a hole provided on the measuring turret E, and being incident on a sensor element 135.

More specifically, the hole 137 is formed in a vertical wall portion of the measuring turret E and in an orthogonal direction to the reaction tube holding axis. The measuring turret E rotates at least 360°, preferably 360° plus one pitch (the next reaction tube-held position), during one intermittent motion of exchange of the reaction tubes by the exchange means in the state of holding the reaction tube 40 so that the measurement by the optical measuring device is applied several times or many times to one reaction tube held by the measuring turret E, whereby measurement precision is improved and the timely change in reaction can be easily measured.

Figure 12:
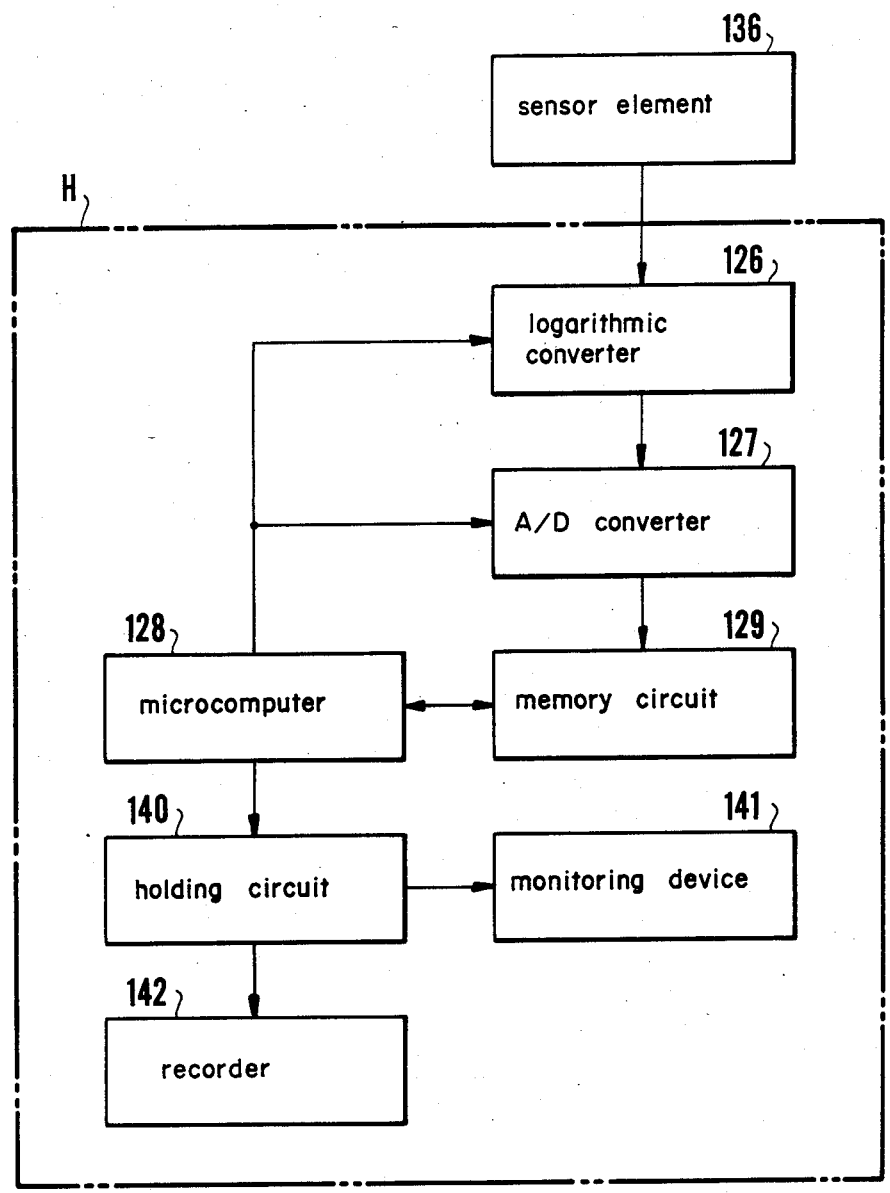
FIG. 12 is a schematic block view illustrating the digital processor.

Thus, the data analyzed by the specific color measurement in the optical device G is input to a digital processor H as illustrated in FIG. 12. The digital processor H comprises a logarithmic converter 126, an A/D converter 127 converting the analysis data input to the logarithmic converter 126 to a digital signal, a microcomputer 128 including a memory circuit 129 which memorizes the digital signal input to the A/D converter 127, a holding circuit 140 holding the memorized and analyzed data of every one specimen measured, a monitoring device indicating the analyzed data of every one measured specimen after measuring a time course of the same specimen, and a recorder 142.

The specific color measurement of the blood specimen held by the measuring turret E is optically made plural times (n times) while the reaction tube 40 is transferred from the measuring position to the cleaning position, and the analyzed data of every one optical measurement on one specimen is transferred to the memory circuit. When the optical measurement is made in plural times (n times) a timely change in the reaction is operated and transferred to the holding circuit 140 for every one specimen and the data necessary for time course display is held for every one specimen. The data held by the holding circuit 140 is displayed as a time course graph in the monitoring device as illustrated in FIG. 13.

The time course graph indicates the analyzed data over plural times (n times) about plural specimens s1, s2, s3, ... sn.

Figure 13:
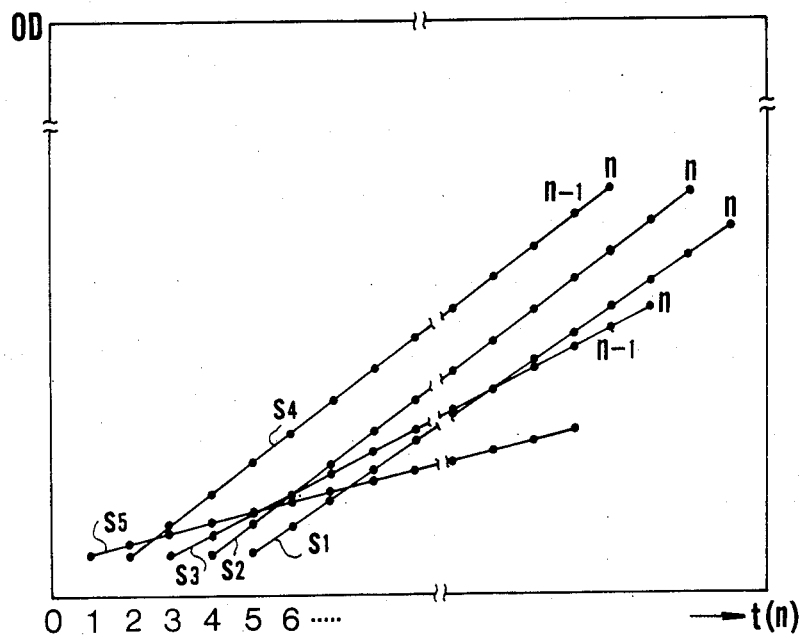
FIG. 13 is a graph showing an analyzed data displayed in a monitoring device.

In FIG. 13, 5 specimens are indicated, in order, for a display area of the monitoring device 141. If one specimen is optically measured for 4 seconds n times, the time course graph for the specimen is displayed for 20 seconds. Thus, after the time course of the specimen s1 goes out, a time course of the sixth specimen s6 is displayed in the monitoring device 141 and successively a time course of sn is displayed.

Therefore, by monitoring a time course of the same specimen, the progress state of reaction of a specimen and the reagent used therewith and a theoretical reaction state can be compared. Further, a record of the time course can be printed by the memory 142, if it is necessary.

The measurement of a specimen explained herein as one embodiment is made by a specific color measurement using an optical means but may be made by a voltage measurement.

The reaction tube 40, after measurement is transferred to and arranged in the feeder B by the reaction tube exchange means J and further transferred to the cleaning means W by the feeder B as described before.

Figure 14:
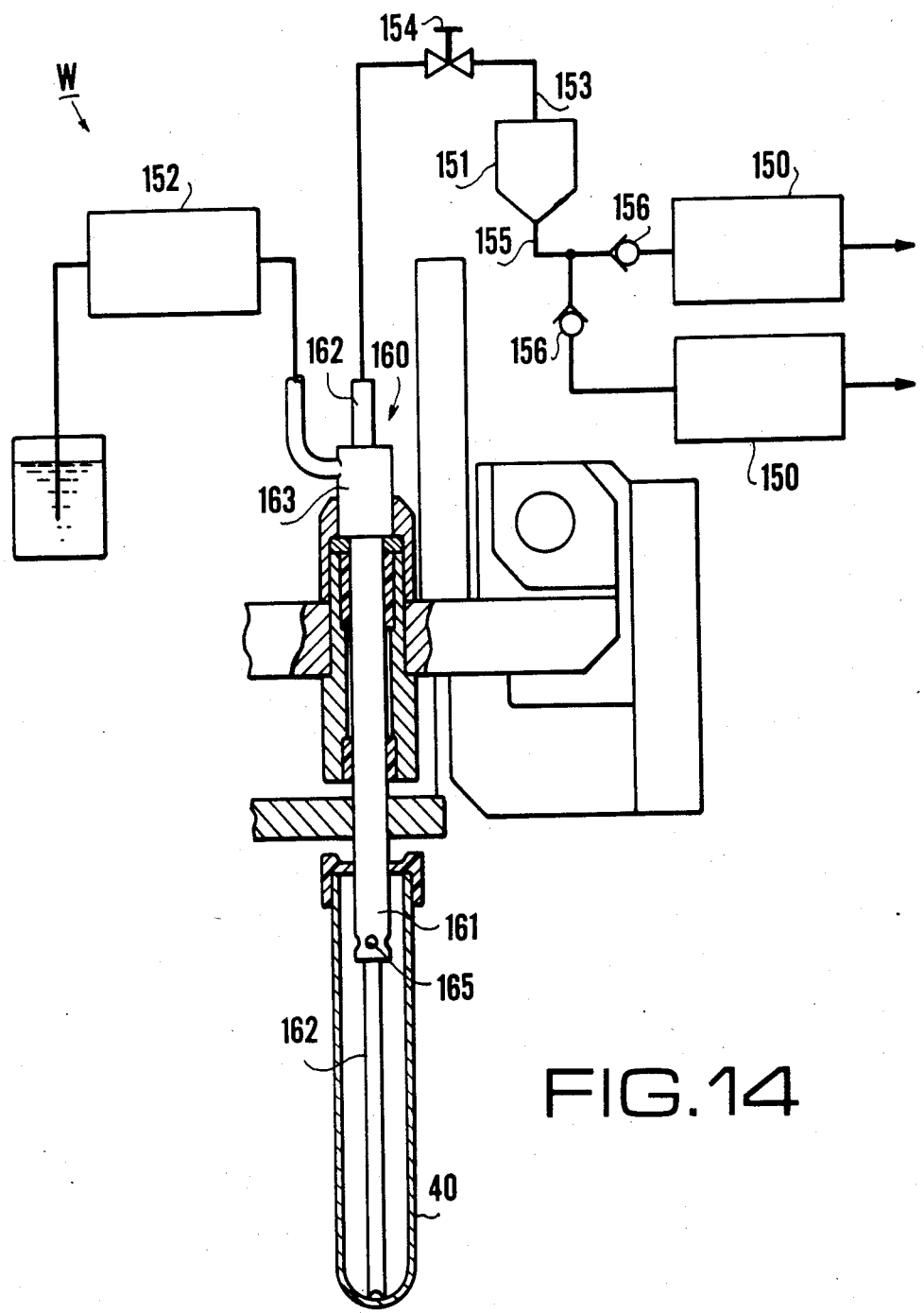
FIG. 14 is a vertical section, partial view illustrating a cleaning device made in accordance with the present invention.

The cleaning means W is comprised, as illustrated in FIG. 14, of two vacuum pumps 150 and 150 sucking and discharging a cleaning treating water, a vacuum tank 151 being connected to the vacuum pump 150, a cleaning nozzle 160 being connected to the vacuum tank 151 and dropping downwardly to the reaction tube 40 at the time of cleaning, a water supply pump 152 hydraulicly supplying cleaning water to the cleaning nozzle 160, an electromagnetic valve 154 disposed in a water pipe 153 being connected to a drain side of the cleaning nozzle 151 and the vacuum tank 160, and check valves 156 and 156 disposed in water pipes 155 being connected to the vacuum pumps 150 and 150 and the vacuum tank 151.

The cleaning nozzle 160 is comprised of a cleaning water charging pipe 161 having a large diameter and a short length, and a cleaning water discharging pipe 162 disposed in the cleaning water charging pipe 161 and having a narrow diameter and long length. The cleaning water discharging pipe 162 is held by a seal material disposed in the opposite end portions of the cleaning water charging pipe 161, in coaxial relation with the cleaning water charging pipe 161. Further in the cleaning water charging pipe 161 at the lower end, a plurality of holes 165 are disposed radially in order to dispense cleaning water toward the inner wall of the reaction tube. The seal placed on the top end of the cleaning water charging pipe 161 has a connecting nozzle which dispenses cleaning water from the water pump 152 to a passage defined by the inner wall of the cleaning water charging pipe 161 and the outer wall of the cleaning water discharging pipe 162.

Thus comprised cleaning means W functions as follows:

First, when the reaction tube 40, after measurement, is transferred to a position just under the cleaning device, the cleaning nozzle 160 is lowered by a lifting means (not shown) and set to start the cleaning.

Next, cleaning water is hydraulicly dispensed into the cleaning water charging pipe 161, then is radially sprayed toward the inner periphery wall of the reaction tube 40 through the holes 165 and flows downwardly to the inner bottom portion of the reaction tube 40 for cleaning out the reactant adhered on the inner periphery wall or suspended matter in the air. Simultaneously with the watering operation of this cleaning water, the vacuum pump for discharging water starts to work so that cleaning water is instantaneously absorbed in the cleaning water discharging pipe 162 with the residue of the reactant or the like and transferred into the vacuum tank 151 and discharged. The cleaning operation may be repeated several times. After the cleaning treatment is finished, the reaction tube 40 is transferred into position to be used again.

It is possible to incorporate an ultrasonic cleaning treatment step in the multiple stage cleaning treatment course by the cleaning nozzle 160 to clean the reaction tube more completely.

What is claimed is:

1. An automatic analytical apparatus for optically measuring a specific color produced by a reaction between a specimen and a reagent, the apparatus comprising:
    at least two parallel rotatable turrets holding circularly arranged therein a plurality of reaction tubes containing specimens and reagents,
    a reagent vessel holder disposed coaxially with one of said at least two turrets and holding circularly arranged therein a plurality of reagent vessels, a first driving means for rotating the reagent vessel holder to bring a selected reagent vessel to a predetermined charging position, charging means for charging reagent from a regent vessel at the charging position into an adjacent reaction tube, reaction tube exchange means for simultaneously exchanging reaction tubes held at a predetermined position in a first one of said at least two turrets for reaction tubes held at a predetermined position in a second one of said at least two turrets, and optical measuring means for optically measuring mixtures of specimen and reagent in the reaction tubes while the reaction tubes are held in the second one of said at least two turrets.

2. An apparatus according to claim 1, wherein the circular arrangement of reagent vessels is radially within the respective circular arrangement of reaction tubes.

3. An apparatus according to claim 1, wherein the reaction tube exchange means is positioned between said at least two reaction tube holding turrets and includes an arm with means at each end thereof for gripping and lifting a reaction tube from each of said at least two turrets, and means for rotating the arm through 180°.

4. An apparatus according to claim 1, comprising a plurality of pipettes in a turret pipette holder and means connected to said turret pipette holder to intermittently rotate and move the pipettes from a specimen sucking position to a pipette cleaning position through a specimen charging position at which a specimen is charged into a respective reaction tube held in the first one of said at least two turrets.

5. An apparatus according to claim 4, wherein there are two specimen sucking positions corresponding to routine and emergency measurements respectively, and each of said pipettes is arranged to suck a specimen at a selected one of these positions.

6. An apparatus according to claim 4, further comprising a second driving means for rotating the reaction tubes held in the second one of said at least two turrets through at least 360° plus one pitch, in synchronism with one stepwise rotation of the reaction tube exchange means.

7. An apparatus according to claim 1, wherein each reagent vessel has a projecting wall portion formed at one part of the vessel in communication with the interior of the vessel.

8. An apparatus according to claim 7, wherein the reagent vessel holder has, adjacent to its center, detecting means which is positioned and arranged to move up and down the projecting wall portion of a respective reagent vessel so as to sense the level of a liquid in the vessel.

9. An apparatus according to claim 8, wherein the projecting wall portion carries indicia relevant to the reagent in the respective vessel.

10. An apparatus according to claim 9, wherein the reagent vessel holder has means for reading said indicia, and said driving means for rotating the reagent vessel holder is responsive to said reading means.

* * * * *

UNITED STATES PATENT AND TRADEMARK OFFICE
CERTIFICATE OF CORRECTION

PATENT NO. : 4,647,432

DATED : March 3, 1987

INVENTOR(S) : KOICHI WAKATAKE

It is certified that error appears in the above-identified patent and that said Letters Patent is hereby corrected as shown below:

On the cover page, Item [73], delete in its entirety and substitute therefor: --- Japan Tectron Instruments Corporation, Tokyo, Japan and Tokuyama Soda Kabushiki Kaisha, Tokuyama, Japan ---.

Signed and Sealed this

Twenty-seventh Day of October, 1987

*Attest:*

DONALD J. QUIGG

*Attesting Officer*  *Commissioner of Patents and Trademarks*

UNITED STATES PATENT AND TRADEMARK OFFICE
CERTIFICATE OF CORRECTION

PATENT NO. : 4,647,432

DATED : March 3, 1987

INVENTOR(S) : Koichi WAKATAKE

It is certified that error appears in the above-identified patent and that said Letters Patent is hereby corrected as shown below:

On the cover page, Item [73], delete in its entirety and substitute therefor: -- Japan Tectron Instruments Corporation, Tokyo, Japan and Olympus Optical Company, Limited, Tokyo, Japan --.

Signed and Sealed this

Ninth Day of February, 1988

Attest:

DONALD J. QUIGG

Attesting Officer

Commissioner of Patents and Trademarks